(12) United States Patent
Holloway et al.

(10) Patent No.: US 6,752,826 B2
(45) Date of Patent: *Jun. 22, 2004

(54) LAYERED STENT-GRAFT AND METHODS OF MAKING THE SAME

(75) Inventors: Ken A. Holloway, Tracy, CA (US); Christofer T. Christoforou, Pleasanton, CA (US)

(73) Assignee: Thoratec Corporation, Pleasanton, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/017,693

(22) Filed: Dec. 14, 2001

(65) Prior Publication Data

US 2003/0114917 A1 Jun. 19, 2003

(51) Int. Cl.[7] .................................................. A61F 2/06
(52) U.S. Cl. ..................................................... 623/1.13
(58) Field of Search .............................. 623/1.13, 1.14, 623/1.32, 1.33, 1.44

(56) References Cited

U.S. PATENT DOCUMENTS

| | | | | |
|---|---|---|---|---|
| 4,604,762 | A | 8/1986 | Robinson | 623/1 |
| 4,731,073 | A | 3/1988 | Robinson | 623/128 |
| 5,123,917 | A | 6/1992 | Lee | 623/1 |
| 5,389,106 | A | 2/1995 | Tower | 606/198 |
| 5,723,004 | A | 3/1998 | Dereume et al. | 623/1 |
| 5,749,880 | A | 5/1998 | Banas et al. | 606/198 |
| 5,779,729 | A | 7/1998 | Severini | 606/191 |
| 6,010,530 | A | 1/2000 | Goicoechea | 623/1 |
| 6,124,523 | A | 9/2000 | Banas et al. | 623/11 |
| 6,139,573 | A | 10/2000 | Sogard et al. | 623/1.13 |
| 6,156,064 | A | 12/2000 | Chouinard | 623/1.44 |
| 6,165,212 | A | 12/2000 | Dereume et al. | 623/1 |

OTHER PUBLICATIONS

Dolmatch, *Healing Response To Vascular Stent–Grafts*, Journal of Vascular Surgery, Jun. 2000, vol. 31, No. 6.

Baldus et al., *Treatment Of Aortocoronary Vein Graft Lesions With Membrane–Covered Stents*, Circulation, 2000; 102:2024–2027.

Monnier et al., *The Use Of The Covered Wallstent For The Palliative Treatment Of Inoperable Tracheobronchial Cancers*, Chest, 1996; 110:5:1161–1168.

Schellhammer et al., *Polyethylene Terephthalate And Polyurethane Coatings For Endovascular Stents: Preliminary Results In Canine Experimental Arteriovenous Fistulas*, Radiology, Apr. 1999, pp. 169–175.

Masakiyo et al., *Restenosis After Percutaneous Transluminal Coronary Angioplast: Pathologic Observations in 20 Patients*, Journal of the American College of Cardiology, Feb. 1991, vol. 17, No. 2, pp 433–439.

Forrester, et al., *A Paradigm for Restenosis Based on Cell Biology: Clues for the Development of New Preventive Therapies*, Journal of the American College of Cardiology, Mar. 1, 1991, vol. 17, No. 3, pp 758–769.

Christodoulos Stefanadis et al., *Stents Covered By Autologous Venous Grafts: Feasibility And Immediate And Long–Term Results*, American Heart Journal, Mar. 2000, vol. 139, No. 3, pp. 437–445.

Eldad Rechavia et al., *Biocompatibility of Polyurethane–Coated Stents: Tissue and Vascular Aspects*, Catheterization and Cardiovascular Diagnosis 45:202–207 (1998).

*Primary Examiner*—Michael H. Thaler

(57) ABSTRACT

A stent-graft made of at least three concentric layers is disclosed. The inner and outer layers can be porous. The middle layer can be non-porous and encompasses a stent.

41 Claims, 8 Drawing Sheets

LAYERED STENT-GRAFT AND METHODS OF MAKING THE SAME

BACKGROUND OF THE INVENTION

1. Field of the Invention

This invention generally relates to implantable intralumenal prostheses. More particularly, this invention relates to intralumenal prostheses having stent frames surrounded by biofunctional graft layers and techniques for manufacturing the same.

2. Description of the Background

Stents-grafts have proven to be an effective medical device for minimally invasive treatment of vascular occlusions such as atherosclerosis and restenosis. Stent-grafts are typically shaped as hollow cylindrical structures and constructed of a metal stent with at least one non-metal coating on the stent. The metal stent provides the stent-graft with a structural framework for mechanical support. Non-metal coatings add any number of functions to the stent-graft including delivery of a drug, prevention of thrombi formation in the stent-graft, and reduction of irritation of the vessel wall as compared with the irritation caused by a bare metal stent.

In U.S. Pat. No. 6,165,212, Dereume et al. teach a supportive endolumenal graft. The graft includes a braided tubular support placed over a liner and under a cover. The support is made of metals or alloys, polymers, or ceramics. Exemplary metals and alloys include stainless steel, titanium, tantalum, nitinol, Elgiloy® and NP35N. Exemplary polymers for making the support include polyurethanes, silicone rubbers, polyether, sulfones, fluoroelastomers, polyimides, polycarbonates, polyethylenes, polylactic acid, polyglycolic acid and polyacrylates. The cover and the liner are made of an elastomeric material, preferably a polyurethane, such as a polycarbonate polyurethane, one commercial example of which is Corethane® (available from Corvita Corporation of Miami, Fla.).

In U.S. Pat. No. 6,139,573, Sogard et al. teach an elongate radially expandable tubular stent and a polymeric layer covering and conforming to the geometry of the external surface of the stent. A polymeric liner layer and the external polymer layer are laminated together to form a composite structure containing the expandable tubular stent so as to form at least three domains of distinct porosity in the device. The stent may be made from a variety of materials including stainless steel, titanium, platinum, gold, and other biocompatible metals. Sogard et al. teach that the polymeric layers are made from expanded polytetrafluoroethylene (ePTFE).

In U.S. Pat. No. 6,010,530, Goicoechea teaches a self-expanding stent encapsulated by a skin. The stent is made of a continuous "zig-zag" nitinol wire wound into a plurality of concentric hoops. The skin is made of an elastomeric polymer, such as Chronoflex (available from PolyMedica Biomaterials Inc., Woburn, Mass.).

In U.S. Pat. No. 5,749,880, Banas et al. teach an encapsulated stent which comprises at least one stent member concentrically interdisposed between at least two tubular ePTFE extrudates, each of the extrudates having a substantially uniaxial fibril microstructure oriented parallel to the longitudinal axis of the stent member.

In U.S. Pat. No. 6,156,064, Chouinard teaches a stent-graft membrane having at least three layers including a structural stent layer, an inside graft layer, and an outside layer. The outside layer is substantially impermeable to fluids. The outside layer is made from a siloxane, polyurethane, polycarbonate urethane, polytetrafluoroethylene (PTFE), ePTFE, or combinations thereof. The graft layer is made from polyethylene tetraphthalate (PET), ePTFE, polycarbonate urethane (PCU), polyurethane, or combinations thereof. The stent filaments may be made of Elgiloy®, Conichrome, Phynox, cobalt-chromium-molybdenum (CoCrMo), titanium alloy, titanium-zirconium-niobium alloy, titanium-aluminum-vanadium alloy (commercially known as TI-6A1-4V), stainless steel, nitinol, platinum, tungsten, tantalum, or combinations thereof.

In U.S. Pat. No. 5,123,917, Lee teaches an expandable intralumenal vascular graft. Lee teaches one embodiment of the graft having an inner layer made from PTFE or a porous polyurethane, an outer layer made of PTFE, Dacron or a proline mesh enclosing the inner layer, and a plurality of spaced scaffold members positioned between the inner layer and the outer layer and made of surgical stainless steel.

In U.S. Pat. No. 5,389,106, Tower teaches a distensible frame and an impermeable deformable membrane interconnecting portions of the frame to form an impermeable exterior wall. The frame is made from a soft platinum wire. The membrane is preferably made from Tactylon® (available from Tactyl Technologies, Inc. of Vista, Calif.).

SUMMARY OF THE INVENTION

In accordance with one aspect of the embodiments of the invention, a stent-graft for biological lumen placement is provided. The stent-graft can include a porous first layer for making contact with tissue of a vessel wall, a non-porous layer substantially encapsulating a frame, and a porous second layer. The non-porous layer can be between the porous first layer and the porous second layer.

In one embodiment of the present invention, the porous first layer can have a void-to-volume ratio of about 40% to about 90%. In another embodiment, the non-porous layer has a void-to-volume ratio of about less than 5%. In yet another embodiment, the porous second layer has a void-to-volume ratio of about 40% to about 90%. In a further embodiment, the pores of the porous first and second layers have an average pore diameter of about 1 micron to about 400 microns.

In accordance with another aspect of the embodiments of the invention, a method for manufacturing a stent-graft is provided. The method of manufacturing can include forming a porous first layer on a mandrel, forming a second layer on the porous first layer, positioning a frame on the second layer, increasing the thickness of the second layer to substantially or completely encapsulate the frame in the second layer, and forming a porous third layer on the second layer.

In one embodiment of the present invention, the act of forming the porous first layer includes applying a composition having a solvent, a polymer dissolved in the solvent, and water-soluble particles to the mandrel and removing the solvent and the water-soluble particles from the polymer. In another embodiment of the present invention, the act of forming the third layer includes applying a composition having a solvent, a polymer dissolved in the solvent, and water-soluble particles to the second layer and removing the solvent and water-soluble particles from the polymer.

DETAILED DESCRIPTION

Figure 1:
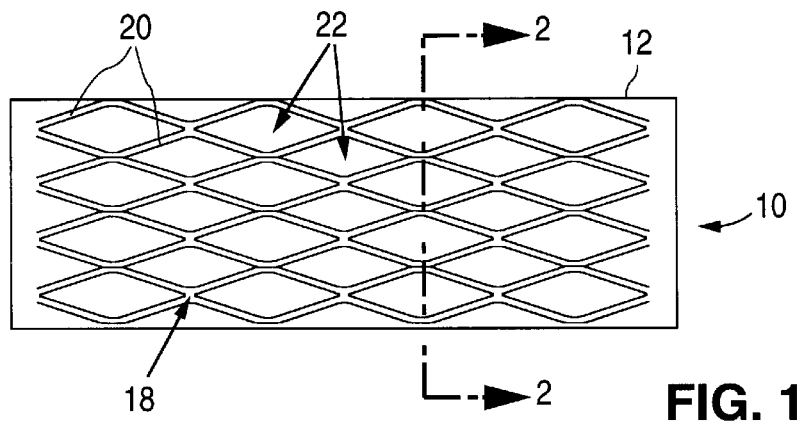
FIG. 1 illustrates a side view of an embodiment of the stent-graft.
Figure 2:
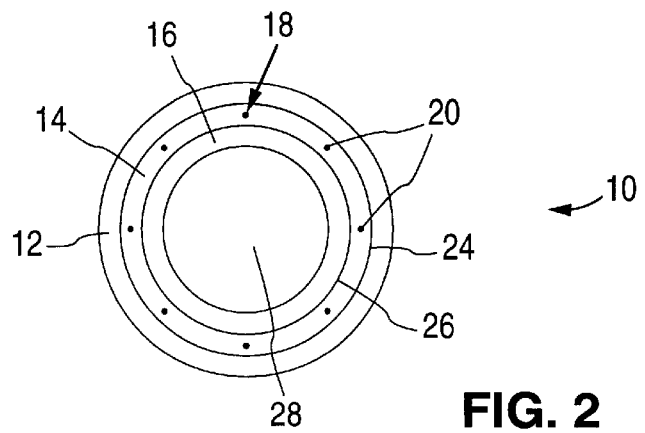
FIG. 2 illustrates cross-section 2—2 of the embodiment of the stent-graft illustrated in FIG. 1.

FIGS. 1 and 2 illustrate one embodiment of a stent-graft 10 including a porous outer layer 12, a non-porous middle layer 14, and a porous lumenal layer 16. The non-porous middle layer 14 contains a stent 18 having struts 20 separated by spaces or voids 22. The division between the porous outer layer 12 and the non-porous middle layer 14 forms an outer seam 24. The division between the non-porous middle layer 14 and the porous lumenal layer 16 forms an inner or lumenal seam 26. The inside of the porous lumenal layer 16 defines a lumen 28.

The stent-graft 10 can have a length of about 1 cm (0.39 in.) to about 10 cm (3.9 in.). In one embodiment, the stent-graft 10 can have a length of about 3 cm (1.2 in.).

Porous Outer Layer

The porous outer layer 12 can be the outer-most layer of the stent-graft 10. The porous outer layer 12 can be generally cylindrical. The porous outer layer 12 can be made of any suitable porous biocompatible material, either bioabsorbable (i.e. biodegradable) or biostable (i.e. non-biodegradable) in nature. Representative examples of materials that can be used include, but are not limited to, any polymeric material including porous polyurethanes (e.g. Thoralon®, available from Thoratec Corporation, Pleasanton, Calif.), ePTFE, PET, alphitic polyoxaesters, polylactides, polycaprolactones, and hydrogels. "Hydrogel" is intended to include a cross-linked polymer, via covalent, ionic, or hydrogen bonding, to form a three-dimensional open lattice structure which is capable of entrapping water molecules to form a gel. Examples of hydrogels include non-permissive hydrogels such as anionic hydrogels (e.g., alginate or carageenan) and "solid" hydrogels (e.g., agarose or polyethylene oxide).

Figure 3:
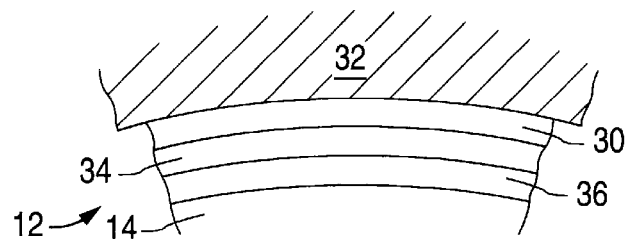
FIG. 3 illustrates a close-up view of a cross-section of an embodiment of the outer porous layer of the stent-graft.

In various embodiments of the stent-graft 10, therapeutic substances can also be contained within the porous outer layer 12 for sustained release of the substrate subsequent to the implantation procedure. Further, the porous outer layer 12 can be made from any number of sub-layers, each having a different porosity. As illustrated in FIG. 3, the outer layer 12 can be made from three sub-layers. A first sub-layer 30 can have a first porosity and can border the intima during use. A second sub-layer 34 can have a second porosity. The third sub-layer 36 can have a third porosity. A plurality of sub-layers made with different porosities can be useful when encouraging different amounts of cell ingrowth and/or different drug release kinetics and rates for the optionally embedded drugs.

Figure 4:
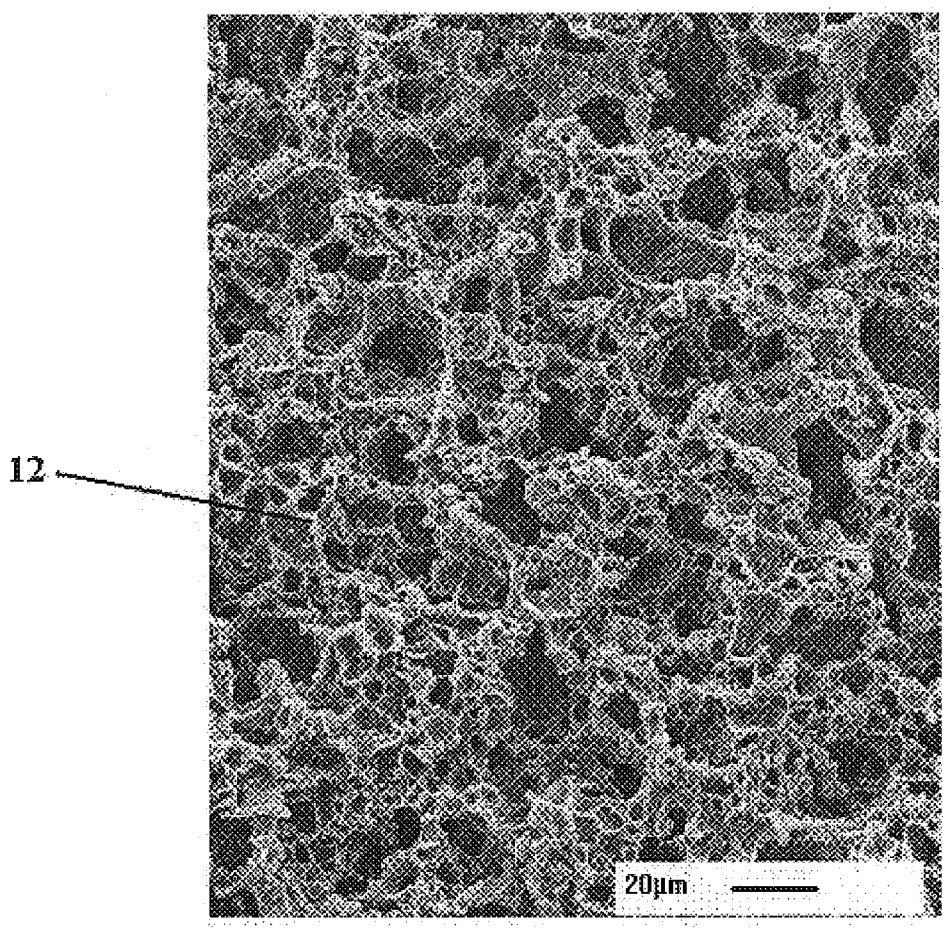
FIG. 4 illustrates a 500 times magnification scanning electron microscope (SEM) image of the surface of an embodiment of the porous outer layer of the stent-graft.

The porous outer layer 12 can have a thickness of about 10 microns (0.39 mils) to about 500 microns (20 mils), more narrowly of about 50 microns (2.0 mils) to about 75 microns (3.0 mils). The outer layer 12 can have a void-to-volume from about 40% to about 90%, more narrowly from about 70% to about 80%, for example about 76%, and a pore diameter from about 1 micron (0.039 mils) to about 400 microns (16 mils), more narrowly from about 1 micron (0.039 mils) to about 75 microns (3.0 mils), including the range of about 1 micron (0.039 mils) to about 38 microns (1.5 mils). "Void-to-volume" is defined as the volume of the pores divided by the total volume of the layer including the volume of the pores. Void-to-volume can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The porosity of the porous outer layer 12 is illustrated by a scanning electron microscope (SEM) image of the surface shown in FIG. 4.

The porous outer layer 12 can function as a platform for allowing intimal growth, anchoring the stent-graft 10 to the vascular intima 32. After implantation of the stent-graft 10, especially implantation in blood vessels, vascular intima 32 can grow into the pores of the porous outer layer 12. Substantially all of the volume of the pores of the porous outer layer 12 can be filled with intimal ingrowth. If vascular intima ingrowth is not desired, the pores can be made from biophobic material or alternatively coated with a chemical that inhibits cell growth, such as non-permissive hydrogels including anionic and "solid" hydrogels. Having the stent-graft 10 not anchor to the vessel wall can also be helpful, especially when the stent-graft 10 is temporary or otherwise intended to be removed. Anchoring, however, can help to prevent migration of the stent-graft 10 after implantation within the body vessel.

The porous outer layer 12 also provides the stent-graft 10 with a lubricious surface to significantly decrease adhesion of the material of the porous outer layer 12 to itself while collapsed (e.g. when pinched and folded or radially compressed) and reduce the degree of friction between the stent-graft 10 and a delivery device. The decreased adhesion and reduced friction can be especially beneficial when the non-porous middle layer's material adheres easily to itself or to the inner surface of the delivery device.

The porous outer layer 12 can also add drug delivery functionality to the stent-graft 10. The porous outer layer 12 can be coated or its pores embedded with any number of drugs. Bioabsorbable chemicals can also be added to the embedded drugs to increase or retard drug delivery rates. The bioabsorption rate of the mixture of the bioabsorbable chemical and the drugs can lie between the bioabsorption rates of the drug by itself and that of the bioabsorbable chemical, thereby speeding or retarding the release rate of the drug. Specific, non-limiting examples of chemicals that can alter drug release rates include alphitic polyoxaesters, polylactides, polycaprolactones, and combinations thereof.

The stent-graft 10 can release pharmaceuticals that prevent implant rejection, counter atherosclerosis and/or restenosis, promote angiogenesis, treat anaphylactic shock, or for other suitable treatment or diagnose purposes. These drugs can be classified as anti-inflammatory, anti-proliferative, anti-migratory, antibiotic, anti-adhesion, and anti-platelet, among others. Drug delivery by the stent-graft 10 can also work symbiotically with the anchoring function discussed above by encouraging intimal cell growth in the pores of the porous outer layer 12.

Non-Porous Middle Layer

Figure 5:
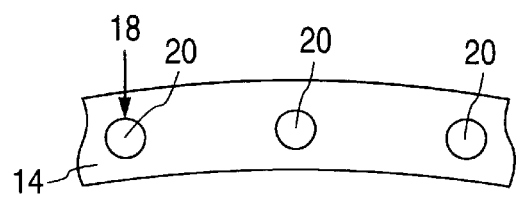
FIG. 5 illustrates a close-up view of a cross-section of an embodiment of the middle non-porous layer of the stent-graft.

The non-porous middle layer 14 can be attached to the porous outer layer 12 and the porous lumenal layer 16. FIG. 5 illustrates the non-porous middle layer 14 encapsulating the stent 18 to provide a seamless polymer layer in which the stent 18 is disposed. Accordingly, the non-porous middle layer 14 can be configured to have no gaps or pockets located around the circumferences of the struts 20, between the polymer layer and the surface of the struts 20.

The non-porous middle layer 14 can be made from any suitable non-porous material that can function to prevent protrusion of the stent 18 from the stent-graft 10, block intimal growth, prevent prolapse of the vessel wall (with some help from the outer and lumenal layers 12 and 16), and, if desired, block drug delivery from the porous outer layer 12 to the lumen 28 and/or from the porous lumenal layer 16 to the intima. Representative examples of materials for the non-porous middle layer 14 include, but are not limited to, any polymeric material including polyurethanes (e.g. Thoralon®), PTFE, alphitic polyoxaesters, polylactides, and polycaprolactones.

Figure 6:
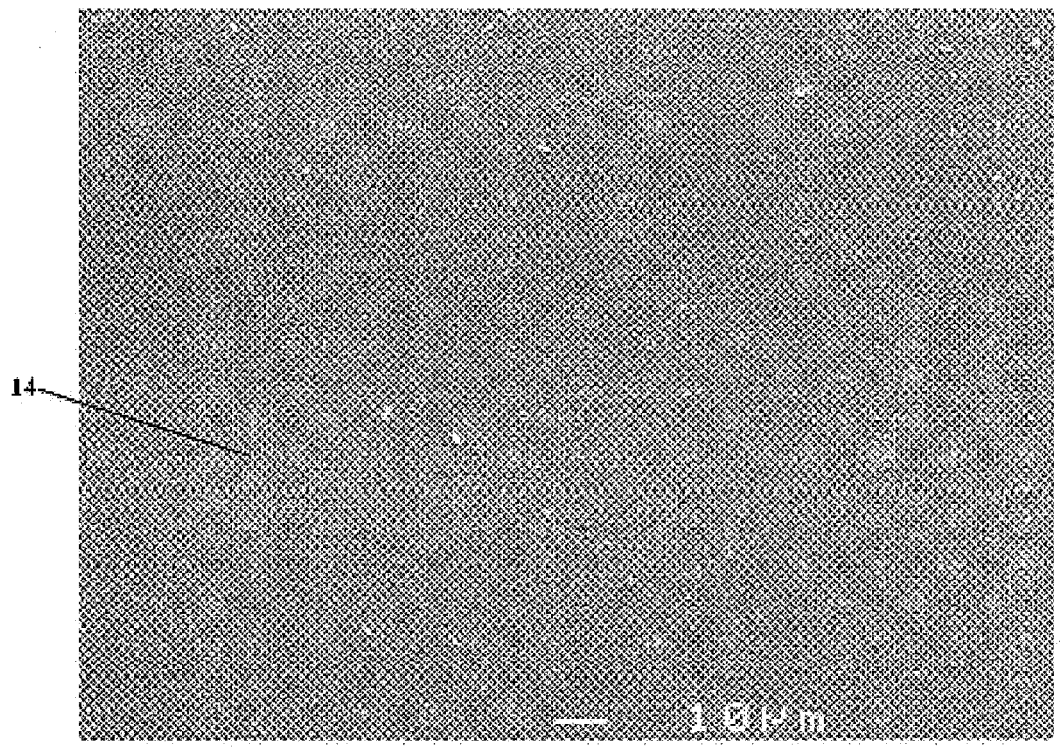
FIG. 6 illustrates a 500 times magnification SEM image of the surface of an embodiment of the non-porous middle layer of the stent-graft.

The non-porous middle layer 14 can have a thickness of about 10 microns (0.39 mils) to about 200 microns (7.9 mils), more narrowly of about 50 microns (2.0 mils) to about 75 microns (3.0 mils). The lack of porosity in the non-porous middle layer 14 can be defined as a void-to-volume of less than about 5%, including less than about 1%. The lack of porosity of the non-porous middle layer 14 is illustrated by an SEM image of the surface shown in FIG. 6.

Porous Lumenal Layer

The porous lumenal layer 16 can be the inner-most radial layer of the stent-graft 10. The porous lumenal layer 16 can be attached to the non-porous middle layer 14. The porous lumenal layer 16 can be made of any suitable porous biocompatible material, either bioabsorbable (i.e. biodegradable) or biostable (e.g. non-biodegradable) in nature. Examples of appropriate materials can be the same as the outer porous layer 12. Similar to the outer porous layer 12, the porous lumenal layer 16 can be designed in sublayers made of different porosity.

Figure 7:
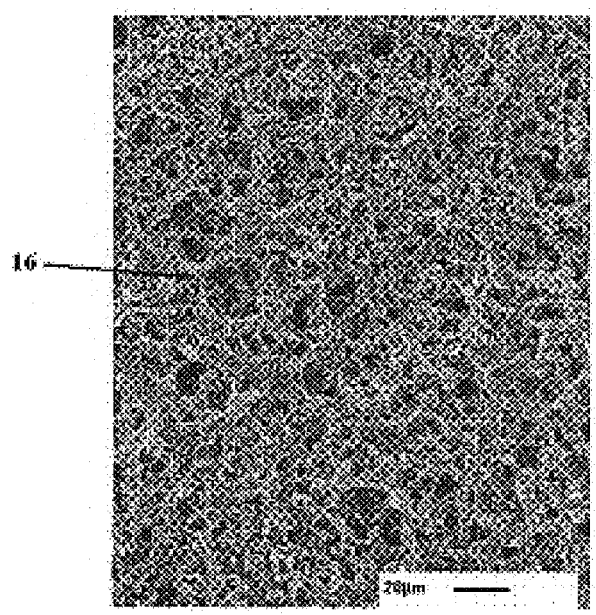
FIG. 7 illustrates a 500 times magnification SEM image of the surface of an embodiment of the porous lumenal layer of the stent-graft.

The porous lumenal layer can have a thickness of about 10 microns (0.39 mils) to about 500 microns (20 mils), more narrowly of about 50 microns (2.0 mils) to about 75 microns (3.0 mils). The lumenal layer 16 can have a void-to-volume from about 40% to about 90%, more narrowly from about 65% to about 80%, for example about 72%, and a pore diameter from about 1 micron (0.039 mils) to about 400 microns (16 mils), more narrowly from about 1 micron (0.039 mils) to about 75 microns (3.0 mils), including the range of about 1 micron (0.039 mils) to about 38 microns (1.5 mils). The porosity of the porous lumenal layer 16 is illustrated by an SEM image of the surface shown in FIG. 7.

The porous lumenal layer 16 can be used for drug delivery by being coated with drugs or having drugs embedded in the matrix. In blood vessels, the porous lumenal layer 16 can deliver drugs directly to the bloodstream in the lumen. The porous lumenal layer 16 can also function as a thromboresistant surface. The porous lumenal layer 16 can be coated or embedded with one or more thromboresistant chemicals such as heparin, prostaglandin, hirudin, urokinase, streptokinase, a sulfated polysaccharide, albumin, fibronectin, laminin, a tissue plasminogen activator, collagen, gelatin, hyalraunic acid, and combinations thereof.

Stent

Figure 8A:
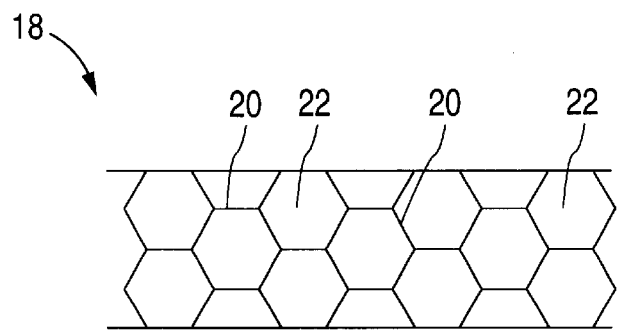
FIGS. 8A–8C illustrate embodiments of a stent used with the stent-graft.
Figure 8B:
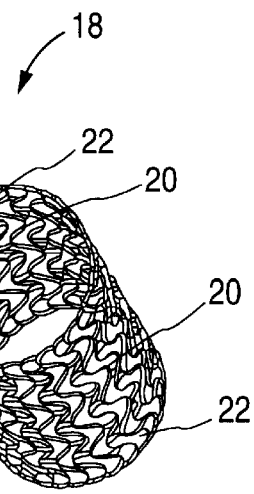
Figure 8C:
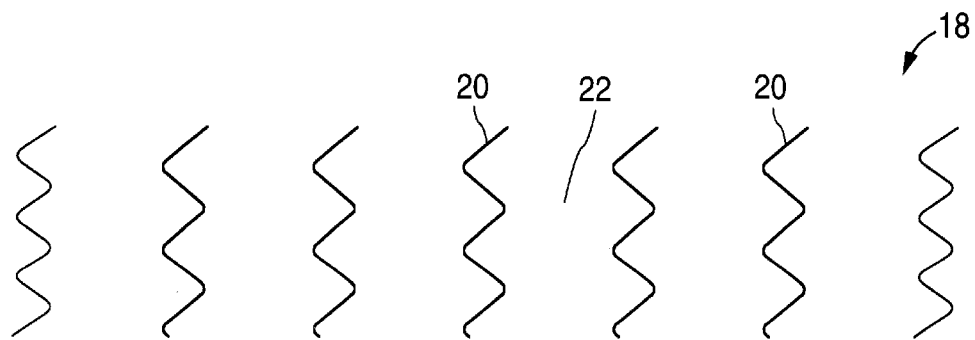

As illustrated in FIGS. 1 and 2, the stent 18 can be entirely surrounded by the non-porous middle layer 14. The stent 18 can have a generally circular cross-section or any other functional cross-sectional geometry such as oval, hexagonal or octagonal. Referring to FIGS. 8A, 8B, and 8C, the stent 18 can be made from a plurality of interconnected (as shown in FIGS. 8A and 8B) or disconnected (as shown in FIG. 8C) struts 20. Junctures between the struts 20 can occur at or between the ends of the struts 20. The junctures can be mechanical crimps, welds, or solder points. The stent 18 can also be machined or etched from a metal cylinder.

Figure 9:
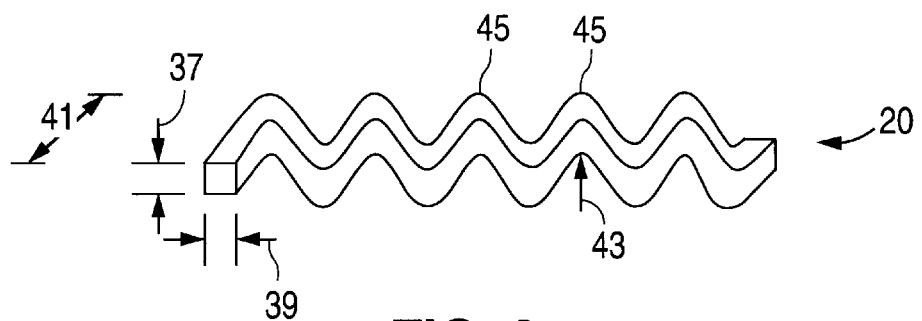
FIG. 9 illustrates a perspective view of an embodiment of a strut used with the stent-graft.

The struts 20 can be straight, curved, or angled. The spaces 22 between the struts 20 can form squares, circles, rectangles, diamonds, as shown in FIG. 1, hexagons, as shown in FIG. 8A, or any other functional geometry. FIG. 9 illustrates an embodiment of a single strut 20 that has been cut and flattened. The strut 20 can have a strut height 37 from about 0.005 mm (0.0002 in.) to about 0.05 mm (0.002 in.), for example about 0.015 mm (0.0006 in.). The strut 20 can have a strut width 39 from about 0.05 mm (0.002 in.) to about 1 mm (0.04 in.), for example about 0.15 mm (0.0059 in.). The strut 20 can have a strut depth 41 from about 1 mm (0.4 in.) to about 10 mm (4 in.), more narrowly about 2.5 mm (0.098 in.) to about 5 mm (0.2 in.). The strut can also have a strut inner radius 43 from about 0.05 mm (0.002 in.) to about 0.5 mm (0.02 in.), for example 0.2 mm (0.008 in.). The strut 20 can have a number of crowns 45 (e.g., from about three to about ten, including about five to about seven). Any number of struts 20 can be used, including the range from about three to about 20, more narrowly about seven.

Figure 10:
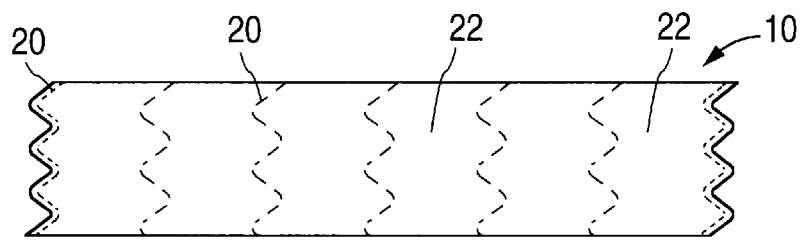
FIG. 10 illustrates a side view of an embodiment of the stent-graft.
Figure 11:
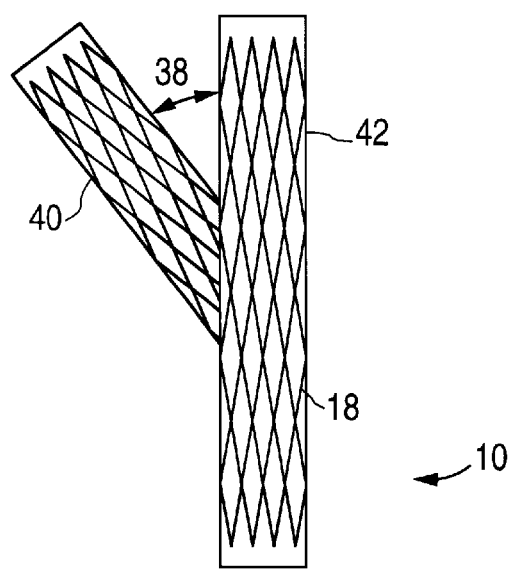
FIG. 11 illustrates a bifurcated embodiment of the stent-graft.

As shown in FIG. 10, disconnected struts 20 can be held in place by the middle layer 14. The layers 12, 14, and 16 at the ends of the stent-graft 10 can also be trimmed to fit the shape of the struts 20, as illustrated in FIG. 10, or trimmed to have generally straight ends, as illustrated by FIG. 1. The spaces 22 between the struts can be small enough or the non-porous middle layer 14 (in combination with the porous lumenal layer 16 and porous outer layer 12) can be strong enough to prevent prolapse. In one embodiment, the ratio of the area covered by the struts 20 to the area of the spaces 22 between the struts 20 can be lower than 15%. The stent 18 can be longitudinally straight or curved with any number of radii of curvature to fit curved body vessels. The stent 18 can also be bifurcated as shown in FIG. 11. A bifurcation angle 38 is the angle between two legs 40 and 42 of a bifurcating stent 18. The bifurcation angle 38 can vary from about 1° to about 90°.

In one embodiment, the stent 18 can be a Symphony® nitinol stent (available from the Medi-Tech division of Boston Scientific Corporation, Natick, Mass.). The stent 18 can be made from other materials including tantalum alloys, cobalt chrome alloys (e.g., Elgiloy®), platinum/tungsten alloys, stainless steels and combinations thereof.

The stent 18 can be foldable to facilitate minimally invasive delivery and deployment of the stent-graft 10. The accompanying layers 12, 14 and 16 of the stent-graft 10 can also be flexible enough to easily fold with the stent 18 during delivery and deployment. The method of folding the stent-graft 10 can include pinching the stent-graft 10 along a longitudinal line and folding the stent-graft 10 over that line, as illustrated in FIGS. 12A–12E and described in detail below.

Figure 12A:
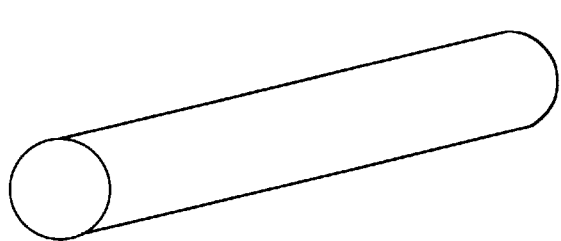
FIGS. 12A–12F illustrate methods of compressing the stent-graft for delivery purposes.
Figure 12B:
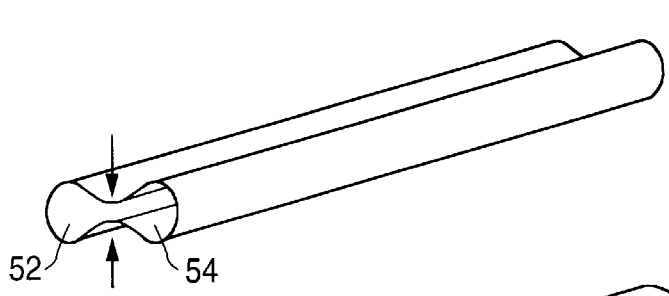
Figure 12C:
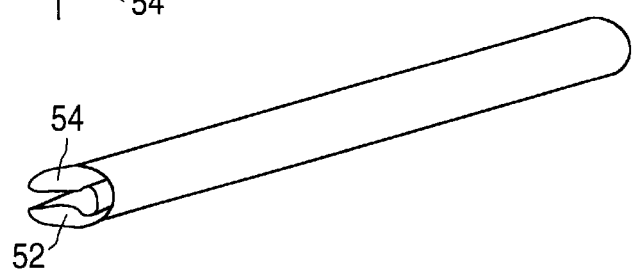
Figure 12D:
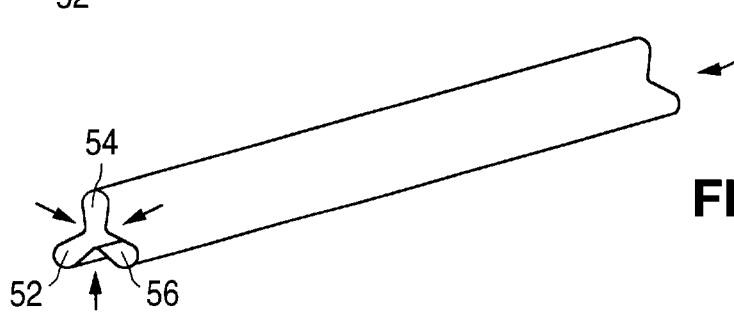
Figure 12E:
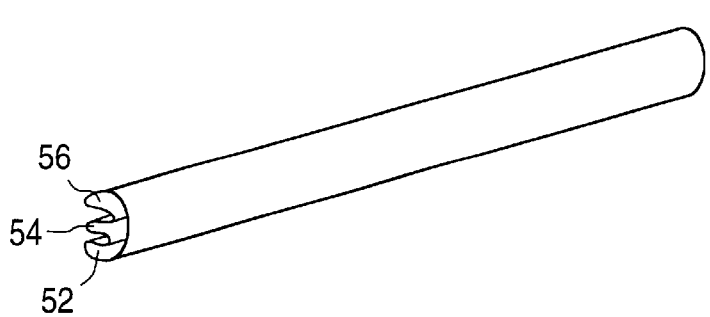
Figure 12F:
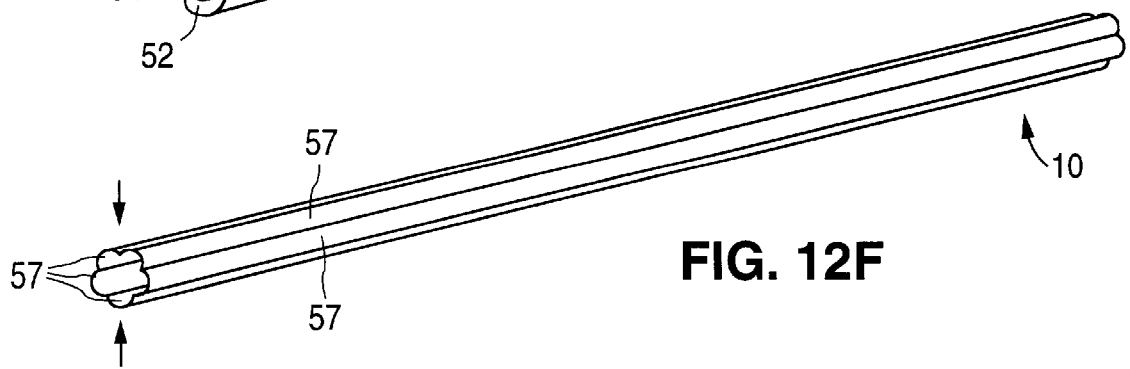

As illustrated in FIG. 12F and described in detail below, the stent 18 can also be radially expandable, such as balloon expandable, self-expandable, or a combination thereof. If a radially expandable stent is used in the stent-graft 10, the outer, middle, and lumenal layers 12, 14 and 16 can bulge out from the spaces 22 between the struts 20 in response to the reduced surface area of the stent-graft 10 when the stent-graft 10 is radially compressed in preparation for delivery.

The stent 18 can include radiopaque markers that improve visibility of the stent 18. Alternatively or in addition to separate radiopaque markers, the struts 20 can themselves be made of a radiopaque material. A radiopaque material can be incorporated into the struts 20, or a radiopaque material can be coated on the struts 20.

Method of Use
Pinching & Folding

FIGS. 12A–12C illustrate an embodiment of a method of folding the stent-graft 10 in preparation for delivery. FIG. 12A illustrates an embodiment of the stent-graft 10 in a normal or relaxed state. In FIG. 12B, a force, shown by the arrows, can be applied to the stent-graft 10 by radial squeezing from two substantially opposite sides of the stent-graft 10. This force causes a pinch in the stent-graft 10. The pinch can extend longitudinally along the substantially entire length of the stent-graft 10. The stent-graft 10 on either sides of the pinch can form rounded lobes 52 and 54. The lobes 52 and 54 also can extend longitudinally along about the substantially entire length of the stent-graft 10.

FIG. 12C illustrates the stent-graft 10 in a pinched and folded state. In this state, the stent-graft 10 can be folded at the pinch along the substantially entire length of the stent-graft 10. This folding can cause the lobes to be pressed and flattened on each other. The pinched and folded stent-graft 10, as illustrated in FIG. 12C, has a smaller cross-sectional area compared with the relaxed stent-graft 10, as illustrated in FIG. 12A to facilitate delivery of the stent-graft 10.

FIGS. 12D and 12E illustrate another embodiment of the method of folding the stent-graft 10. FIG. 12D illustrates the stent-graft pinched, shown by the arrows, along three lines to create three lobes 52, 54, and 56. As illustrated in FIG. 12E, the three lobes 52, 54 and 56 can then be folded upon each other.

Accordingly, the stent-graft 10, after pinching and folding, can be inserted into a delivery device, which would allow the stent-graft 10 to be delivered into lumens with small cross-sectional areas. Release of the foldable stent-graft 10 from the delivery device causes the stent-graft 10 to regain its original relaxed shape of FIG. 12A.

Radially Compressing

FIG. 12F illustrates a radially compressible embodiment of preparing the stent-graft 10 for delivery. The radially expandable stent-graft 10 can be balloon expandable or self-expandable. In one embodiment, the radially expandable stent-graft 10 can be compressed by applying two or more inward radial forces, shown by the arrows, on the stent-graft 10. Because of the radially compressible construction of the stent 18, several embodiments of which are known to one having ordinary skill in the art, the stent-graft 10 collapses to a smaller diameter.

When the stent-graft 10 is radially compressed, the layers 12, 14, and 16 can be flexible enough to collapse into the center of the stent-graft or extend out from the stent-graft 10 forming numerous bulges 57. The bulges 57 need not be longitudinally continuous as shown in FIG. 12F, and can generally mimic the shape of the voids 22 in the stent 18.

The radially compressible stent-graft 10 can be deployed via any suitable delivery device, such as a dilatation catheter. The stent-graft 10 can be inserted into a body vessel by any method known to one having ordinary skill in the art. A typical method for stent-graft insertion includes compressing or folding of the stent-graft 10 and loading it onto a delivery catheter or delivery guidewire. The delivery catheter or guidewire can then be fed through a percutaneous delivery device, such as an introducer or trocar, into the vasculature. Delivery can also be made without a percutaneous delivery device when the stent-graft 10 is deployed to an easily accessible location such as the esophagus.

Method of Manufacture

All of the compositions can be prepared by conventional methods where all components are combined then blended. For example, a predetermined amount of a polymer or a combination of polymers is dissolved in a solvent or a combination of solvents in, for example, an anhydrous condition at ambient pressure. If necessary, gentle heating and agitation, such as by stirring, can be employed to effect dissolution of the polymer. A solvent is defined as any fluid capable of placing the polymer into a solution at the desired concentration.

Porous Lumenal Layer

An inert (e.g., glass) mandrel can facilitate manufacturing of the stent-graft 10. In one embodiment, the mandrel can be 6 mm (0.24 in.) in diameter and can be cleaned before manufacturing with isopropyl alcohol. The mandrel can be immersed in a first composition or, alternatively, the mandrel can be sprayed with the first composition for forming the porous lumenal layer 16.

The first composition can constitute at least one of the aforementioned polymers admixed with a first solvent. Any suitable solvent for the polymer can be used as the first solvent including alcohols and aromatic hydrocarbons. One specific example of a suitable solvent is dimethyl acetamide (DMAC). Using Thoralon® as the polymer and DMAC as the solvent, the composition can comprise about 5% to about 40% polymer by weight. Different levels of polymer within the range can be used to fine tune the viscosity needed for any given process. The first composition can include less than 5% polymer for some spray application embodiments. In one embodiment where the mandrel is immersed in the first composition, the first composition can be about 14% polymer by weight.

Porosity can be introduced by adding water-soluble particles, such as salt, to the composition before the composition is applied to the mandrel. In one embodiment, the particles can be mixed into the composition with a spinning blade mixer for about an hour under ambient pressure and in a temperature range of about 18° C. to about 27° C. The particles can then be extracted by soaking the dried layer in distilled water and dissolving the particles, leaving pores behind. The resulting void-to-volume can be substantially equal to the ratio of salt volume to the volume of the polymer plus the salt. The resulting pore diameter can also be substantially equal to the diameter of the salt grains. Extraction can occur through a variety of methods known to those having ordinary skill in the art, including soaking in substantially still water at 60° C. for one hour while on a mandrel, and soaking in substantially still water at 60° C. for one hour while off the mandrel. Extraction can occur once all the layers and the stent have been applied. The first composition can have an amount of salt of about 10 to about 20 times, for example about 14 times, the amount of polymer by weight.

In one embodiment, the mandrel can be immersed in the first composition at a speed of about 70 cm/min (28 in./min) through a die (having, for example, a diameter of about 6.76 mm (0.266 in.)). Subsequent to the application of the first composition, the first solvent can be removed or allowed to evaporate to form a film layer of the polymer on the mandrel. Evaporation can be induced by application of heat treatment, for example, about 5 minutes to about 24 hours in an oven at about 25° C. to about 80° C. For example, heat treatment can be conducted at about 60° C. for about 20 minutes at ambient pressure. Alternatively, vacuum conditions can be employed. The process of application of the first composition and removal of the first solvent can be repeated to form the porous lumenal layer 16 of any suitable thickness.

Non-porous Middle Layer and Stent

Subsequent to the formation of the porous lumenal layer 16, a second composition can be applied to the porous lumenal layer 16 for deposition of the non-porous middle layer 14 by spraying or immersing the mandrel. The second composition can constitute at least one of the aforementioned polymers for the non-porous middle layer 14 admixed with a second solvent. The second solvent can be the same as or different than the first solvent. The second solvent can wet the lumenal layer 16 to aid bonding with the middle layer 14. The possible ratio of polymer to solvent for the second composition can be the same as the ratio for the first composition. In one embodiment where the mandrel is immersed in the second composition, the second composition can be about 24% polymer by weight.

In one embodiment, the step of removing the solvent of the porous lumenal layer 16 need not be taken to a completion, so as to provide a porous lumenal layer 16 with a semi-solid surface. The semi-solid surface can provide a better adhesive tie between the lumenal layer 16 and the middle layer 14, in essence, eliminating a distinct seam between the two layers 14 and 16.

In one embodiment, the mandrel can be immersed in the second composition at a speed of about 70 cm/min (28 in./min) through a die (having, for example, a diameter of about 6.76 mm (0.266 in.)). Subsequent to the application of the second composition, the second solvent can be removed or allowed to evaporate to form a film layer of the polymer on the lumenal layer 16. Evaporation can be induced by the application of heat treatment, for example, about 5 minutes to about 24 hours in an oven at about 25° C. to about 80° C. For example, then heat treatment can be conducted at about 60° C. for 60 minutes at ambient pressure. Alternatively, vacuum conditions can be employed.

Following the formation of a layer of the non-porous middle layer 14, the stent 18 can be placed on the mandrel and securely positioned on the non-porous middle layer 14. The second composition can then be applied again to encapsulate the sent 18. In one embodiment, this second application of the second composition can be performed by immersing the mandrel in the second composition at a speed of about 70 cm/min (28 in./min) through a die (having, for example, a diameter of about 7.24 mm (0.285 in.)).

Subsequent to the application of the second composition for encapsulating the stent 18, the second solvent can be removed or allowed to evaporate. Evaporation can be induced by application of heat treatment, for example, about 5 minutes to about 24 hours in an oven at about 25° C. to about 80° C. For example, the heat treatment can be conducted at about 60° C. for about 30 minutes at ambient pressure. Alternatively, vacuum conditions can be employed. The process of application of the second composition and removal of the second solvent can be repeated to form the non-porous middle layer 14 of any suitable thickness.

The expanded shape of the stent 18 can be pre-set in an annealing process before the stent 18 is positioned on the mandrel. Prior to positioning the stent 18 on the non-porous middle layer 14, the stent 18 can be mounted on a mandrel simulating the desired final shape of the stent 18. The stent 18 can then be heated for a time and at a temperature to increase grain size and then cooled to recrystalize the stent material in a desired phase. The mechanical properties of the stent 18, including modulus of elasticity and plateau stress, can vary based on the heat treatment time and temperature. The stent material and dimensions can also be determinative of the annealing time and temperature. For example, a nitinol stent on a reshaping mandrel can be heat treated at 460° C. for 15 minutes. A nitinol stent on a reshaping mandrel can, however, also be heat treated at 460° C. for 5 minutes, thus producing different mechanical characteristics of the stent including a higher modulus of elasticity and plateau stress than the stent heated for 15 minutes. Annealing times and temperatures for different materials and producing different results are known to one having ordinary skill in the art.

Porous Outer Layer

Subsequent to the formation of the non-porous middle layer 14, a third composition can be applied to the non-porous middle layer 14 for forming of the porous outer layer 12. The third composition can constitute at least one of the aforementioned polymers for the porous outer layer 12 admixed with a third solvent. The third solvent can be the same as or different that the first or second solvent. The third solvent can wet the middle layer 14 to aid bonding with the outer layer 12. The possible ratio of polymer to solvent for the third composition can be the same as the ratio for the first composition. In one embodiment where the mandrel is immersed in the third composition, the third composition can be about 10% polymer by weight.

The third composition can also include particles to form pores. The third composition can have an amount of salt about 1 to about 10 times, for example about 6 times, the amount of polymer by weight.

In one embodiment, the mandrel can be immersed in the third composition at a speed of about 70 cm/min (28 in./min) through a die with about a 7.24 mm (0.285 in.) diameter. Subsequent to the application of the third composition, the third solvent can be removed or allowed to evaporate to form a film layer of the polymer on the mandrel. Evaporation can be induced by application of heat treatment, as described for the first composition. Alternatively, vacuum conditions can be employed. The process of application of the third composition and removal of the third solvent can be repeated to form the porous outer layer 12 of any suitable thickness.

Coatings and Drugs

The stent-graft 10 can also be coated on the lumenal side or the outer side by spraying with or dipping in coating chemicals which can be mixed in a removable solvent. Lubricants can be incorporated in coatings including silicones, polyvinyl pryoladone, and polypropylene oxide (PPO), and any other bio-compatible lubricants known to one having ordinary skill in the art. Drugs may also be incorporated as a coating or embedded in the porous layers 12 and 16. The drugs can be in dissolution, either saturated or supersaturated, within the solvent and polymer composition or suspended in fine particles. Alternatively, drugs can be physically incorporated into the pores of the outer layer 12 and the lumenal layer 16.

EXAMPLES

The invention will be better understood by making reference to the following examples which are being provided by way of illustration and are not intended to unduly limit the scope of the invention. In each example, an embodiment of the stent-graft was tested for different characteristics. The stent-grafts used in the examples were Symphony® nitinol stents coated with an approximately 110 micron thick porous lumenal layer, an approximately 135 micron thick nonporous middle layer, and an approximately 205 micron thick porous outer layer, all of which were made from Thoralon®.

Example 1-Durability Testing

Three stent-grafts were loaded into lumens of mock arteries that had radial compliance similar to human arteries (e.g., 5–7% radial compliance) and subjected to accelerated durability testing. Durability testing was performed in an EnduraTEC testing system (available from EnduraTEC Systems Corp., Minnetonka, Minn.) filled with water at 37° C. Pressure was cycled from 80 mmHg diastolic to 120 mmHg systolic at a rate of 40 Hz for 56 hours. This is equivalent to 77 days at a heart rate of 72 beats per minute. At the completion of the durability run, each stent-graft was visually inspected at 40× magnification for tears in the covering, stent protrusion, delamination of the covering, stent failure or any other obvious device failure. No failures were evident in any of the stent-grafts at the completion of the testing.

Example 2-Deployment Testing

Experiments to evaluate the delivery systems and their ability to properly deploy the stent-graft were performed in a mock artery with 5% to 7% radial compliance in a flow loop with a 10F sheath introducer (available from Cordis Corp., Miami, Fla.). A Thoratec® 14086 ventricular assist device (VAD) gave a flow rate through the mock arteries between 180 and 220 ml per minute through the target vessel at 72 beats per minute. Three stent-grafts were loaded into separate delivery systems and steam sterilized for 35 minutes at 120° C.

To simulate in vivo deployment conditions, deployments were performed with a covering over the mock arteries to blind the operator during the delivery. Each stent-graft was deployed through the introducer into a mock artery by advancing the introducer into position and retracting an outer sheath on the introducer. The introducer was then withdrawn. If the delivery system did not completely deploy the device or was not able to be withdrawn, deployment was considered a failure. A visual inspection determined that all three devices deployed properly.

Example 3-Migration Testing

Following the deployment testing, in the same system, the location of each stent-graft was marked on the outer vessel and flow continued for three days. If any movement was noted, the test was considered a failure. At the end of testing the location of each device was determined by visual inspection and no migration was evident.

Example 4-Metal Ion Oxidation (MIO) Testing

MIO testing was performed to determine if Thoralon® would degrade in the presence of nitinol. The MIO testing used both negative (theoretically no damage) and positive (theoretically severe damage) controls along with the test samples (nitinol stents encapsulated within a middle layer of Thoralon®, but with no outer or inner layer). Samples were immersed in a solution of 3% hydrogen peroxide at 37° C. for extended periods of time. Degradation was assessed through visual examination and molecular weight analysis. If degradation occurred, the molecular weight of the samples would decrease and stress cracks in the polymer would form. Samples were removed and tested every two weeks. Testing out to 15 weeks showed degradation of the positive controls while the test stent-grafts and negative controls showed no evidence of degradation.

Example 5-Animal Study

Three stent-grafts were tested in the carotid arteries of three sheep along with three control stents for 30 days. The effect of the stent-graft to maintain a dilated vessel, prevent thrombus formation, promote ingrowth of intima, and remain structurally intact, among other characteristics, is demonstrated by these in vivo studies. Table 1 summarizes the animal study.

TABLE 1

| Animal Number | Carotid Vessel | Pre-Implant Diameter (mm) | PreExplant Diameter (mm) | Test Article |
|---|---|---|---|---|
| 1 | Right | 5.0 | 5.5–6.0 | Stent-graft |
|   | Left | 4.8 | 5.5–6.0 | Bare stent |
| 2 | Right | 4.8 | 5.7 | Bare stent |
|   | Left | 5.3 | 5.5 | Stent-graft |

The animal studies were performed at Covance Research products (CRP) under IACUC protocol IAC-578. Angiograms of the animals' carotids were first obtained. The carotids were then separated from the surrounding tissue and the blood flow through the carotids was constricted. Then the carotids were accessed by a 9F introducer sheath in an incision about 7 cm in length and about 15 cm distal to the deployment site. Stent-grafts of 6 mm internal diameter were then implanted and deployed into each animal's larger carotid using a stent-graft delivery system. The stent-grafts were placed in the larger of the two carotids in each animal to allow for more accurate sizing. The delivery system and introducer sheath were then removed. The puncture site was then closed using 7-0 prolene ensuring a good closure with no leakage, and post-implant angiograms were taken. The animals were maintained on a standard diet and care and give daily aspirin for 30 days. After 30 days, angiograms were taken again, vessel diameter measurements were obtained, the animals were euthanized and the carotid arteries and test devices were removed, preserved in formalin, sectioned and stained.

In Animal 1, pre-explant diameter data taken from the angiogram suggested vessel diameters on both sides larger than the maximum stent diameter. Thus this data was disregarded. Internal diameters read from histological sections show internal diameters at explant of about 5.5 mm to about 6.0 mm.

Figure 13:
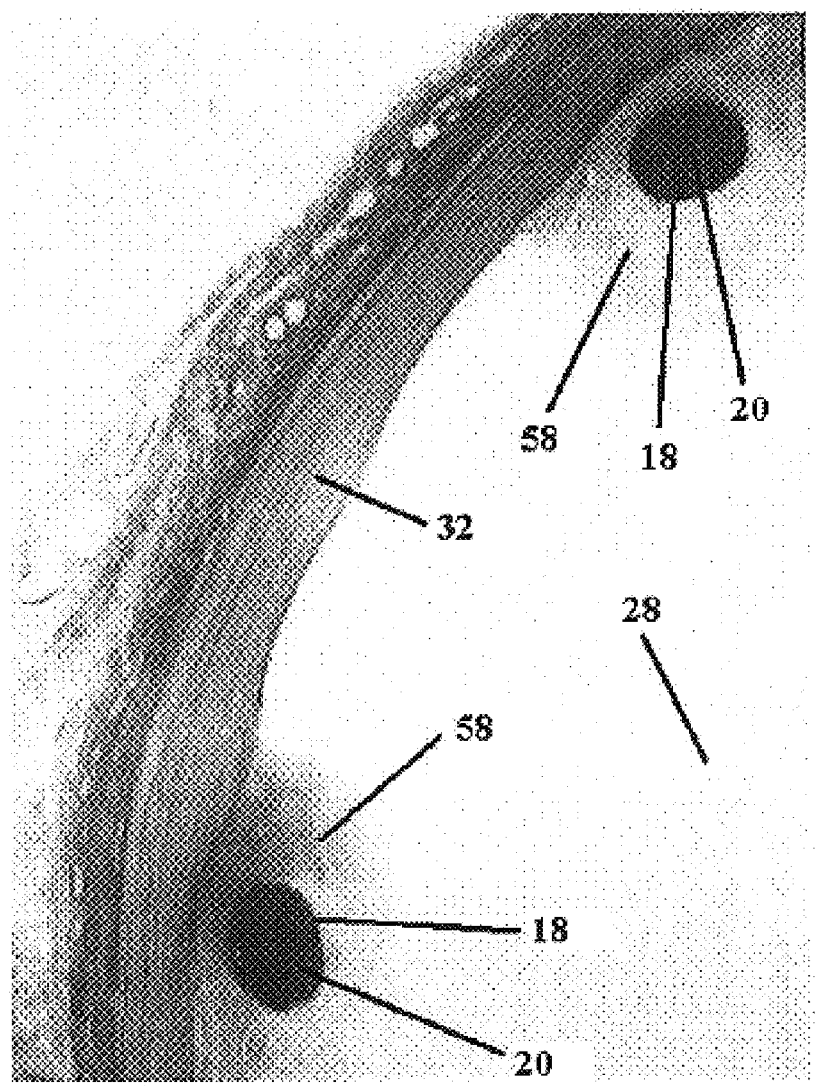
FIG. 13 illustrates a 40 times magnification histology slide from an animal study using a bare stent as a control.

FIG. 13 shows a 40 times magnified close-up of the histological slide for the vessel and a control stent of Animal 1. A portion of an intima 32 of a vessel is shown with cross-sections of the stent 18 pressed against it. Both cross-sections of the stent 18 are surrounded by large masses of thrombi 58. This control result shows an occurrence of thrombi 58 with the uncoated stent. Furthermore, there is no ingrowth of the intima 32 into the stent 18. The stent 18 is even separated from the intima 32 by the thrombi 58. Signs of prolapse between the struts 20 of the stent 18 are also present.

Figure 14:
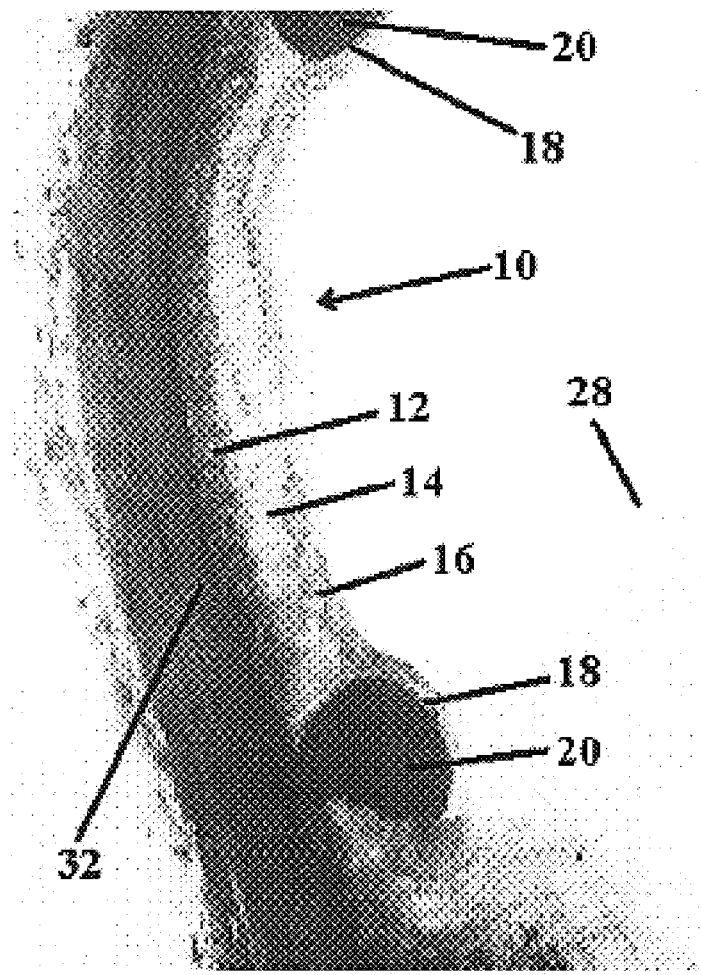
FIG. 14 illustrates a 40 times magnification histology slide from an animal study using an embodiment of the stent-graft.

FIG. 14 shows a 40 times magnified close-up of the histological slide for the vessel and stent-graft 10 of Animal 1. FIG. 14 shows positive results. Thrombi in the lumen along the surface of the porous lumenal layer 16 are not detectable, especially with respect to the control. In fact, the porous lumenal layer 16 has no signs of tissue proliferation at all. Ingrowth of the intima 32 along the outer porous layer 12 is plentiful, highlighted by the darkened color of the outer porous layer 12. Higher magnifications of the vessel also showed no inflammatory reaction to the stent-graft 10 and no platelet adhesion or other signs of thrombus formation. Further, there are no signs of prolapse along the intima 32.

Animal 2 produced good pre-implant and pre-explant diameter measurements. The diameter measurements shown above in Table 1 illustrate that both the stent-graft and the stent significantly dilate the vessel, hold structural integrity, and prevent occlusion. Due to Animal 2 having a smaller carotid pre-implant diameter and only one size of the stent and the stent-graft available for the study, the stent-graft was constricted so much that the cramped layers folded slightly into the lumen. With a proper sized stent-graft, this would probably not be a problem. Histological slides from Animal 2 concur with the results from the histological slides from Animal 1. Even with the minimal obstruction of the lumen by the folded layers of the improperly sized stent-graft, the porous lumenal layer 16 still had no signs of thrombi or other tissue proliferation. The control stent, however, still produced thrombi. The porous outer layer 12 had good ingrowth of the intima and prolapse with the stent-graft was non-detectable, yet visible in the vessel with the control stent. (Slides for Animal 2 are not shown to prevent misinterpretation due to distortion from air bubbles created during slide preparation and the folds of the layers into the lumen.)

Although the invention has been disclosed in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A stent-graft comprising:
an intraluminal implantable body configured for percutaneous intraluminal delivery into a vessel, the intraluminal implantable body comprising a porous first layer having an outer surface, the entire longitudinal length of the outer surface of the porous first layer is adapted to make contact with tissue of a vessel wall; a non-porous layer attached to the porous first layer; a self expandable. balloon expandable or combination of self expandable and balloon expandable stent, for allowing the stent-graft to expand to a suitable diameter to compress the porous first layer against a vessel wall such that the stent is mechanically supporting the vessel wall, encapsulated by the non-porous layer; and a porous second layer attached to the non-porous layer having the stent, the porous second layer having an inner surface that is adapted to make contact with bodily fluids that flow through a longitudinal bore of the stent-graft wherein the stent-graft includes (i) a compressed configuration that allows the stent-graft to be delivered percutaneouly and intraluminally into a vessel by a catheter and/or a guide wire and maneuvered along a vascular network to a delivery site and (ii) expanded configuration, substantially greater in outer diameter than the compressed configuration that allows the stent-graft to be secured inside of a vessel, and wherein the thickness of the combination of the layers is of a suitable size that does not adversely affect the flow of fluid through the vessel.

2. The stent-graft of claim 1, wherein the porous first layer has a void-to-volume ratio of about 40% to about 90%.

3. The stent-graft of claim 1, wherein the porous first layer has a void-to-volume ratio of about 70% to about 80%.

4. The stent-graft of claim 1, wherein the non-porous layer has a void-to-volume ratio of about less than 5%.

5. The stent-graft of claim 1, wherein the non-porous layer has a void-to-volume ratio of about less than 1%.

6. The stent-graft of claim 1, wherein the porous second layer has a void-to-volume ratio of about 40% to about 90%.

7. The stent-graft of claim 1, wherein the porous second layer has a void-to-volume ratio of about 65% to about 80%.

8. The stent-graft of claim 1, wherein pores of the porous first and second layers have an average pore diameter of about 1 micron to about 400 microns.

9. The stent-graft of claim 1, wherein the stent comprises a plurality of interconnected struts separated by gaps.

10. The stent-graft of claim 1, wherein the stent comprises a plurality of rings separated at a distance from one another.

11. The stent-graft of claim 1, wherein the porous first or second layer comprises a plurality of sub-layers, each sub-layer having a different porosity.

12. The stent-graft of claim 1, wherein the porous first layer is made from a hydrogel.

13. The stent-graft of claim 1, wherein the porous first layer is bioabsorbable or biodegradable so as to absorb or degrade in a lumen after a duration of time.

14. The stent-graft of claim 1, wherein the porous second layer is bioabsorbable or biodegradable so as to absorb or degrade in a lumen after a duration of time.

15. The stent-graft of claim 1, wherein the stent-graft is capable of folding in half along a longitudinal axis of the stent-graft.

16. The stent-graft of claim 1, wherein the stent-graft is capable of folding over at least three times along a longitudinal axis of the stent-graft.

17. The stent-graft of claim 1, wherein the outer surface of the porous first layer is lubricious.

18. The stent-graft of claim 1, wherein the outer surface of the porous first layer is not capable of sticking to itself when the stent-graft is crimped to a smaller diameter or folded along a longitudinal axis of the stent-graft.

19. The stent-graft of claim 1, wherein the pores of the second layer contain thromboresistant chemicals.

20. The stent-graft of claim 1, wherein the porous first layer includes an anionic hydrogel.

21. The stent-graft of claim 1, wherein the porous first layer includes a chemical that inhibits cell growth or is made from a material that inhibits cell growth.

22. The stent-graft of claim 1, wherein the non-porous layer does not include a seam at the junction where the stent is encapsulated in the non-porous layer.

23. The stent-graft of claim 1, wherein the stent-graft includes a bifurcated portion.

24. The stent-graft of claim 1, wherein pores of the porous first and second layers have an average pore diameter of about 150 micron to about 400 microns.

25. The stent-graft of claim 1, wherein the porous first layer allows for intimal growth within the first layer so as to anchor the stent-graft within a vessel lumen.

26. The stent-graft of claim 1, wherein the porous first layer has a thickness of about 50 microns to about 75 microns.

27. The stent-graft of claim 1, wherein the porous second layer has a thickness of about 50 microns to about 75 microns.

28. The stent-graft of claim 1, wherein the porous second layer is made from a hydrogel.

29. A method of manufacturing a intraluminal stent-graft comprising:
  (a) forming a porous first layer on a mandrel, the porous first layer being the inner most layer of the intraluminal stent-graft such that an inner surface of the porous first layer is configured to be exposed to bodily fluids that travel through a longitudinal bore of the intraluminal stent-graft;
  (b) forming a non-porous second layer on the porous first layer;
  (c) positioning a stent on the non-porous second layer;
  (d) increasing the thickness of the non-porous second layer to substantially or completely encapsulate the stent in the non-porous second layer; and
  (e) forming a porous third layer on the non-porous second layer, the porous third layer being the outermost layer of the intraluminal stent-graft and configured to make contact with a wall of the vessel, wherein the stent-graft is of a suitable dimension to allow for percutaneous insertion of the stent-graft within a lumen of a patient, wherein the stent-graft includes a compressed configuration that allows the entire length of the stent-graft to be delivered percutaneouly into a vessel by a catheter and/or a guide wire and a deployed, expanded configuration, substantially greater in diameter than the compressed configuration, that allows the stent-graft to be implanted within a vessel and wherein the thickness of the combination of the layers is of a suitable size that does not adversely affect the flow of fluid through the vessel.

30. The method of claim 29, wherein the act of forming the porous first layer comprises applying a composition comprising a solvent, a polymer dissolved in the solvent, and water-soluble particles added thereto to the mandrel and removing the solvent and the water-soluble particles from the polymer.

31. The method of claim 30, wherein the water-soluble particles are removed subsequent to removal of the solvent.

32. The method of claim 29, wherein the act of forming the third layer comprises applying a composition comprising a solvent, a polymer dissolved in the solvent, and water-soluble particles added thereto to the second layer and removing the solvent and water-soluble particles from the polymer.

33. The method of claim 32, wherein the water-soluble particles are removed subsequent to removal of the solvent.

34. The method of claim 29, wherein the porous first and third layers have a void-to-volume ratio of about 40% to about 90%.

35. The method of claim 29, wherein the second layer has a void-to-volume ratio of less than about 5%.

36. The method of claim 29, wherein the stent comprises a plurality of interconnected struts.

37. The method of claim 29, wherein the stent comprises a plurality of rings separated at a distance from one another.

38. The method of claim 29, wherein the second layer does not include any gapped regions about the area where the second layer is in contact with the surfaces of the stent.

39. The method of claim 29, wherein the acts of (a) and (b) comprise:
  (a) applying a first composition comprising a first polymer and a first solvent to the mandrel and removing most of the first solvent from the first composition to solidify the first polymer on the mandrel but allowing the surface of the first polymer to be in a semi-sold state;
  (b) applying a second composition comprising a second polymer and a second solvent to the first polymer and removing the first and second solvents to form the first layer and the second layer attached to the first layer.

40. The method of claim 29, wherein the acts of (b) through (e) comprise:
  (a) applying a first composition comprising a first polymer and a first solvent to the first layer and removing essentially all of the first solvent from the first composition to solidify the first polymer for the second layer;
  (b) positioning the stent on the second layer;
  (c) reapplying the first composition to the second layer and the stent and removing the first solvent from the first composition to increase the thickness of the second layer;
  (d) repeating act (c) if needed until the stent is substantially or completely encapsulated by the second layer; and
  (e) applying a second composition comprising a second polymer and a second solvent to the second layer to form the third layer.

41. The method of claim 40, wherein the second composition is applied to the second layer having a semi-solid surface.

* * * * *